United States Patent
Cully et al.

(10) Patent No.: US 10,039,660 B2
(45) Date of Patent: Aug. 7, 2018

(54) SPACE-FILLING DEVICE (71) Applicant: W.L. Gore & Associates, Inc., Newark, DE (US)

(72) Inventors: Edward H. Cully, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 231 days.

(21) Appl. No.: 15/015,677

(22) Filed: Feb. 4, 2016

(65) Prior Publication Data

US 2016/0151186 A1 Jun. 2, 2016

Related U.S. Application Data

(62) Division of application No. 13/955,220, filed on Jul. 31, 2013, now Pat. No. 9,277,905.

(Continued)

(51) Int. Cl.
*A61M 29/00* (2006.01)
*A61F 5/00* (2006.01)
(Continued)

(52) U.S. Cl.
CPC .......... *A61F 5/003* (2013.01); *A61B 17/0057* (2013.01); *A61B 17/12109* (2013.01);
(Continued)

(58) Field of Classification Search
CPC ........ A61B 17/12002; A61B 17/12186; A61B 17/1219; A61B 17/1215;
(Continued)

(56) References Cited

U.S. PATENT DOCUMENTS

| 4,395,806 A | 8/1983 | Wonder et al. |
|---|---|---|
| 5,334,210 A | 8/1994 | Gianturco |

(Continued)

FOREIGN PATENT DOCUMENTS

| JP | 2006-223579 A | 8/2006 |
|---|---|---|
| JP | 4061337 | 12/2007 |

(Continued)

OTHER PUBLICATIONS

International Application No. PCT/US2012/049465, International Preliminary Report on Patentability dated Feb. 20, 2014, 13 pages.

(Continued)

*Primary Examiner* — Katherine M Shi
(74) *Attorney, Agent, or Firm* — Kilpatrick Townsend & Stockton, LLP (57) ABSTRACT

A medical device includes a vessel member, a port that couples a compartment interior of the vessel member to a region exterior of the vessel member, and a tubular member that defines a lumen. A distal end of the tubular member is attached to an internal surface of the vessel member within the compartment so that a portion of the internal surface of the vessel member provides a seal at a distal end of the lumen. The tubular member passes through the port, and the proximal end of the tubular member is configured to remain exterior of the compartment. A delivery of a sufficient amount of a filling material into the lumen of the tubular member causes a length of the tubular member to pass through the port and into the vessel compartment.

18 Claims, 4 Drawing Sheets

Related U.S. Application Data (60) Provisional application No. 61/799,939, filed on Mar. 15, 2013, provisional application No. 61/678,898, filed on Aug. 2, 2012.

(51) Int. Cl.
  *A61B 17/00* (2006.01)
  *A61B 90/00* (2016.01)
  *A61B 17/12* (2006.01)
  *A61B 17/02* (2006.01)
  *A61M 25/00* (2006.01)

(52) U.S. Cl.
  CPC ........ *A61B 17/12136* (2013.01); *A61B 90/02* (2016.02); *A61F 5/0036* (2013.01); *A61B 17/1214* (2013.01); *A61B 17/1219* (2013.01); *A61B 17/12099* (2013.01); *A61B 17/12113* (2013.01); *A61B 17/12122* (2013.01); *A61B 17/12186* (2013.01); *A61B 2017/00632* (2013.01); *A61B 2017/00654* (2013.01); *A61B 2017/00818* (2013.01); *A61B 2017/00858* (2013.01); *A61B 2017/00893* (2013.01); *A61B 2017/0225* (2013.01); *A61B 2017/1205* (2013.01); *A61M 25/00* (2013.01)

(58) Field of Classification Search
  CPC ...... A61B 2017/1205; A61B 17/12136; A61B 17/12113; A61B 17/12145; A61B 17/12109; A61B 17/12172; A61B 17/12131; A61B 17/12031; A61B 17/12036; A61B 17/1204; A61B 2017/00818; A61F 5/0036; A61F 5/003
  USPC ................................. 606/191, 194, 198, 200
  See application file for complete search history.

(56) References Cited

U.S. PATENT DOCUMENTS

| | | | |
|---|---|---|---|
| 5,634,895 | A | 6/1997 | Igo et al. |
| 6,328,749 | B1 | 12/2001 | Kalmann et al. |
| 6,440,098 | B1 | 8/2002 | Lüscher |
| 6,589,199 | B1 | 7/2003 | McCrory et al. |
| 7,049,380 | B1 | 5/2006 | Chang et al. |
| 7,462,675 | B2 | 12/2008 | Chang et al. |
| 7,892,201 | B1 | 2/2011 | Laguna et al. |
| 8,048,440 | B2 | 11/2011 | Chang et al. |
| 8,075,582 | B2 | 12/2011 | Lointier et al. |
| 9,055,949 | B2 | 6/2015 | Belfort et al. |
| 9,277,905 | B2 | 3/2016 | Cully et al. |
| 2002/0026217 | A1 | 2/2002 | Baker et al. |
| 2002/0052653 | A1 | 5/2002 | Durgin |
| 2003/0167069 | A1 | 9/2003 | Gonzales et al. |
| 2003/0181931 | A1 | 9/2003 | Dieck et al. |
| 2003/0216685 | A1 | 11/2003 | Porter |
| 2004/0049210 | A1 | 3/2004 | VanTassel et al. |
| 2005/0033409 | A1 | 2/2005 | Burke et al. |
| 2005/0085836 | A1 | 4/2005 | Raymond |
| 2005/0090861 | A1 | 4/2005 | Porter |
| 2005/0133046 | A1 | 6/2005 | Becker et al. |
| 2006/0058829 | A1 | 3/2006 | Sampson et al. |
| 2006/0161197 | A1 | 7/2006 | Paul et al. |
| 2006/0178696 | A1 | 8/2006 | Porter et al. |
| 2006/0206139 | A1* | 9/2006 | Tekulve ........... A61B 17/12022 606/200 |
| 2006/0271154 | A1* | 11/2006 | Woodall ........... A61B 17/12136 623/1.11 |
| 2007/0078480 | A1 | 4/2007 | Belenkaya et al. |
| 2007/0082021 | A1 | 4/2007 | Bates |
| 2007/0083187 | A1 | 4/2007 | Eversull et al. |
| 2007/0142859 | A1 | 6/2007 | Buiser et al. |
| 2008/0109027 | A1 | 5/2008 | Chen et al. |
| 2009/0028923 | A1 | 1/2009 | Muni et al. |
| 2009/0069883 | A1 | 3/2009 | Ding et al. |
| 2009/0118761 | A1 | 5/2009 | Masters et al. |
| 2009/0275973 | A1 | 11/2009 | Chen et al. |
| 2009/0287231 | A1 | 11/2009 | Brooks et al. |
| 2009/0312593 | A1 | 12/2009 | Drobnik et al. |
| 2009/0312807 | A1 | 12/2009 | Boudreault et al. |
| 2010/0130998 | A1 | 5/2010 | Alverdy |
| 2010/0256667 | A1 | 10/2010 | Ashby et al. |
| 2011/0178544 | A1 | 7/2011 | Sosnowski et al. |
| 2012/0184978 | A1 | 7/2012 | Witts et al. |
| 2013/0035665 | A1 | 2/2013 | Chu et al. |
| 2014/0031850 | A1 | 1/2014 | Bouasaysy et al. |

FOREIGN PATENT DOCUMENTS

| | | |
|---|---|---|
| WO | 9719643 | 6/1997 |
| WO | WO-01/95833 A2 | 12/2001 |
| WO | 2006047748 | 5/2006 |
| WO | 2007073549 | 6/2007 |
| WO | 2007094374 | 8/2007 |
| WO | 2007095125 | 8/2007 |
| WO | WO-2008/117257 A2 | 10/2008 |
| WO | 2008147861 | 12/2008 |
| WO | 2009009466 | 1/2009 |
| WO | 2009070686 | 6/2009 |
| WO | 2009132141 | 10/2009 |
| WO | WO-2011/112713 A2 | 9/2011 |

OTHER PUBLICATIONS

International Application No. PCT/US2012/049465, International Search Report and Written Opinion dated Mar. 13, 2013, 21 pages.
International Application No. PCT/US2012/049465, Invitation to Pay Additional Fees mailed on Oct. 18, 2012, 8 pages.
International Application No. PCT/US2013/053294, International Search Report and Written Opinion dated Dec. 11, 2013, 16 pages.

* cited by examiner

SPACE-FILLING DEVICE

CROSS-REFERENCE TO RELATED APPLICATIONS

This application is a divisional application of U.S. patent application Ser. No. 13/955,220, filed on Jul. 31, 2013, which claims the benefit of priority under 35 U.S.C. § 119(e) to U.S. Patent Application Nos. 61/678,898, filed on Aug. 2, 2012 and 61/799,939, filed on Mar. 15, 2013, the entire contents of each are hereby incorporated by reference.

TECHNICAL FIELD

The present disclosure relates to deployable space-filling medical devices, including space-filling balloon devices that may be implanted within an organ, a cavity, an aperture, an intra-tissue site, a tissue void space, or a conduit within a patient, and to methods of making and deploying the devices.

BACKGROUND

Space-filling devices are useful for filling or occupying void regions within the human body. One example of a space-filling device is a medical implant that is implanted in a stomach of a patient to suppress the patient's appetite. Feelings of hunger can be affected by the degree to which the stomach is filled, where feelings of hunger may be related to an amount of available or empty space within the stomach. For example, a person's appetite may be relatively low when empty space within the stomach is relatively small or minimized. By contrast, the person may have an increased appetite when empty space within the stomach is relatively larger. Increased appetite or feelings of hunger can lead to increased food consumption, which over time can lead to weight gain for the person. By contrast, decreased appetite can lead to decreased food consumption, which over time can lead to weight loss for the person. Thus, weight loss may be promoted by reducing or occupying a volume of void space in the stomach to decrease appetite. Other strategies for reducing the stomach volume include placing a gastric band on the stomach, and restructuring the gastrointestinal tract with a gastric bypass.

Void regions within the human body can also contribute to pathologies and undesirable physiological states. For example, a thrombus in a void region of a left atrial appendage (LAA) can be a contributor to strokes. For example, during abnormal cardiac cycles (e.g., cardiac cycles characterized by arrhythmias such as atrial fibrillation), the LAA may fail to sufficiently contract, which can allow blood to stagnate within the LAA. Stagnant blood within the LAA is susceptible to coagulation and forming a thrombus, which can dislodge from the LAA and ultimately result in an embolic stroke. In some instances, thrombus formation in the LAA can be minimized by occluding the LAA with an occlusion device that is placed within the LAA and that fills the cavity of the LAA, or with an occlusion device that is placed across the ostium of the LAA (the opening between the left atrium and the LAA) to seal the LAA.

Aneurysms provide another example of a void region that can be associated with undesirable physiological effects. Aneurysms often occur when part of a blood vessel or cardiac chamber swells and defines a cavity, either because of damage to, or weakness of, tissue in the area of the aneurysm. Left untreated, pressure within a cavity of the aneurysm may cause the aneurysm to rupture, which can lead to a hemorrhagic stroke. In some instances, aneurysms may be treated by clipping a neck region of the aneurysm to close off the cavity of the aneurysm, by filling the cavity of the aneurysm with a material to block the cavity, or by filling the cavity of the aneurysm with a material that eliminates the aneurysm by initiating a clotting reaction within the cavity of the aneurysm.

SUMMARY

In one general aspect, a medical device includes a vessel member, such as a balloon member, that defines a compartment interior (also referred to herein as interior compartment, internal compartment, or compartment) of the balloon member, where the vessel member is configured to be inserted into a cavity in a body. The vessel member comprises an interior compartment and a port that defines a passage from the interior compartment to the exterior of the vessel member. In various embodiments, the vessel member can have elastic or distensive properties that allow the vessel to be filled as illustrated herein in a number of embodiments. In some embodiments the balloon is enlarged by filling. For illustrative purposes, a balloon member is utilized to describe various embodiments herein, although other vessel members are contemplated and described. The medical device also includes a port, where the port couples the compartment interior of the balloon member to a region exterior of the balloon member. In some embodiments, the port can be a separate component attached to the balloon member. In some embodiments, the port can be an integral part of the balloon member. The medical device further includes a tubular member that defines a lumen and includes a distal end and a proximal end, the distal end of the tubular member being fixed, such as by attachment or coupling, to an internal surface of the balloon member within the compartment so that a portion of the internal surface of the balloon member provides a seal at a distal end of the lumen. In some embodiments a benefit to the fixation of the distal end of the tubular member is a reduction or elimination of potential knotting of the tubular member. The tubular member passes through the port, and the proximal end of the tubular member is configured to remain exterior of the compartment. In some embodiments, the tubular member is operable to fill the interior of the balloon member by advancement of the tubular member into the compartment interior of the balloon member. In some embodiments the tubular member is operable to fill the interior of the balloon member by addition of a filling material to the lumen of the tubular member.

In various implementations, delivery of a sufficient amount of a filling material into the lumen may cause a substantial length of the tubular member to pass through the port and into the compartment interior of the balloon member, the filling material being contained within the lumen of the tubular member. The filling material may include a solid, a liquid, a gas, a foam, or a gel. The filling material may include a saline solution or silicone. The filling material may include a radiopaque material. The filling material may include at least one of a bioinert material and a biocompatible material. The filling material may include a first reagent and a second reagent, the second reagent being functional to activate the first reagent. The medical device may further include at least one anchoring member attached to an exterior surface of the balloon member, and the anchoring member may include a hook, a barb, or an atraumatic end. The medical device may further include a stopping member that is adapted to engage the proximal end of the tubular member, wherein at least a portion of the stopping member is sized larger than an opening of the port such that when engaged to the proximal end of the tubular member, the proximal end of the tubular member is prevented from passing through the port and into the compartment. At least a portion of an outer surface of the balloon member may include a stiff surface region, which may surround the port. The medical device may occupy a first volume prior to delivering the filling material into the lumen of the tubular member, and may occupy a second volume after delivering the filling material into the lumen of the tubular member, the second volume being greater than the first volume. A buoyancy of the medical device may be adjustable. The lumen of the tubular member may carry a first filling material that includes a solid, a liquid, a gas, a foam, or a gel, and the buoyancy of the balloon may be reduced by delivering a further filling material including a liquid into the lumen of the tubular member, or may be increased by delivering a further filling material including a gas into the lumen of the tubular member. The buoyancy may be adjusted by delivering one or more liquids, solids, gasses, foams or gels into the lumen of the tubular member. The medical device may be adapted to be disposed in an organ, a cavity, an aperture, an intra-tissue site, a tissue void space, including, for example, a stomach, a left atrial appendage, or an aneurysm. The medical device may be adapted to occlude a vessel, to expand tissue for transplant for reconstructive purposes, or to be disposed in a wound. The tubular member may include fluorinated polymers and copolymers and expanded fluorinated polymers and copolymers including, for example, expanded polytetrafluoroethylene (ePTFE). The vessel member, such as a balloon member, may be distensible, or may be non-distensible. The proximal end of the tubular member may be prevented from passing through the port such that the proximal end of the tubular member remains external to the interior compartment. The medical device may further include a delivery catheter that delivers the filling material to the lumen of the tubular member. In some embodiments the medical device may include a delivery catheter that advances the tubular member into the compartment interior of vessel member with or without filling the lumen of the tubular member. In some embodiments, application of a force to at least a portion of the tubular member urges a length of the tubular member into the compartment interior of the balloon. The tubular member may be sized to be disposed at least partially within the delivery catheter. The delivery catheter may be sized to be disposed at least partially within the tubular member. The delivery catheter may extend into the compartment interior of the balloon member to deliver the filling material into the lumen of the tubular member.

In a second general aspect, a medical device includes a balloon member that defines a compartment interior of the balloon member, the balloon member being configured to be inserted into a cavity in a body. The medical device also includes a port attached to the balloon member, where the port couples the compartment interior of the balloon member to a region exterior of the balloon member. The medical device further includes a tubular member that defines a lumen and includes a distal end and a proximal end, the distal end of the tubular member being fixed or otherwise attached to an internal surface of the balloon member within the compartment so that a portion of the internal surface of the balloon member provides a seal at a distal end of the lumen. The tubular member passes through the port, and the proximal end of the tubular member is configured to remain exterior of the compartment. The tubular member is configured to be filled by a filling material delivered into the lumen of the tubular member.

In a third general aspect, a system includes a medical device that includes a balloon member that defines a compartment interior of the balloon member and is configured to be inserted into a cavity in a body, a port, and a tubular member. The port is attached to the balloon member, and couples the compartment interior of the balloon member to a region exterior of the balloon member. The tubular member defines a lumen and includes a distal end and a proximal end, where the distal end of the tubular member is attached to an internal surface of the balloon member within the compartment so that a portion of the internal surface of the balloon member provides a seal at a distal end of the lumen. The tubular member passes through the port, the proximal end of the tubular member is configured to remain exterior of the compartment, and the tubular member is configured to be filled by a filling material delivered into the lumen of the tubular member. The system also includes a delivery catheter that is adapted to couple with at least the proximal end of the tubular member, the delivery catheter providing a conduit that delivers the filling material into the lumen of the tubular member. The system further includes a pressurized filling material delivery apparatus that is configured to deliver the filling material into the delivery catheter.

In a fourth general aspect, a method of filling a cavity within a body of a patient includes delivering a medical device to the cavity, where the medical device is configured to occupy at least a portion of the cavity. The medical device includes a balloon member that defines a compartment interior of the balloon member and is configured to be inserted into a cavity in a body and a port attached to the balloon member, where the port couples the compartment interior of the balloon member to a region exterior of the balloon member. The medical device also includes a tubular member that defines a lumen and includes a distal end and a proximal end, the distal end of the tubular member being attached to an internal surface of the balloon member within the compartment so that a portion of the internal surface of the balloon member provides a seal at a distal end of the lumen. The tubular member passes through the port, and the proximal end of the tubular member is configured to remain exterior of the compartment. The tubular member is configured to be filled by a filling material delivered into the lumen of the tubular member. The method also includes delivering the filling material into the lumen of the tubular member.

Some embodiments can include one or more of the following advantages. In some examples, the structure of the space-filling device may provide the space-filling device with a low profile, which may substantially prevent or reduce the extent to which the space-filling device may potentially cause an obstruction near the delivery site at which the space-filling device is implanted, as compared to potential obstructions caused by alternative space-filling devices. The low profile of the space-filling device may further provide for easier navigation to a delivery site, and later for easier removal or repositioning of the space-filling device from the delivery or deployment site. The ability to remove both filler and device through the endoscope may also be advantageous. Adjustable buoyancy is an advantage due to increased patient comfort.

In some examples, the balloon member may be distensible such that the balloon member, can stretch to accommodate an additional portion of the tubular member (as compared to a portion that would be accommodated by a non-distensible balloon member) and thereby conform to a size of a cavity, void, or aperture at the delivery site. The tubular member may be made of a material that is sufficiently flexible, conformable, and compliant such that the tubular member can be thrust beyond the distal end of the delivery catheter and into the internal compartment of the balloon member as a filler substance is delivered into the lumen of the tubular member via the delivery catheter. As the tubular member is thrust into the internal compartment of the balloon member, the flexibility, conformability, and compliance of the tubular member may allow the tubular member to fold (e.g., jumble) upon itself to randomly pack and fit within the internal compartment of the balloon member. The tubular member may further be constructed of a material that has a tensile strength sufficient to allow the tubular member to be easily removed (e.g., pulled) by its proximal end, away from the delivery site, without tearing, necking, or otherwise mechanically failing. The tubular member may also be distensible. A first delivery force can be used to deploy the tubular member into the balloon member, and a second delivery force (e.g., a greater or higher delivery force with respect to the first delivery force) can be used to distend the tubular member. In this embodiment, the same length tube can occupy a greater volume.

During implantation of the space-filling device, after a desired amount of the filling material has been delivered into the lumen of the tubular member, after a desired length of the tubular member has been delivered into the balloon member, or both, the delivery catheter may be removed from the proximal region of the tubular member, and the proximal region of the tubular member remaining external to the balloon member may be effectively sealed, for example with a tie, cap, or the proximal portion may seal upon itself. As a result of at least a portion of the proximal region of the tubular member remaining external to the port of the balloon member following filling of the tubular member, and because a distal portion of the tubular member is attached to the balloon member, the tubular member may be prevented from knotting upon itself within the internal compartment of the balloon member. At an appropriate time following implantation of the space-filling device, the space-filling device may be easily and atraumatically removed from the delivery site by pulling the portion of the tubular member remaining external of the balloon member to urge portions of the tubular member within the balloon member through the port and outside of the balloon member until the tubular member extends substantially out of the port of the balloon member, and the balloon member accordingly everts. In some embodiments the vessel member can collapse or fold sufficiently to allow recovery via a catheter.

Other aspects, features, and advantages will be apparent from the description, the drawings, and the claims.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

Like reference symbols in the various drawings indicate like elements. It should also be noted that the accompanying drawing figures referred to herein are not all drawn to scale and may be exaggerated to illustrate various aspects of the present disclosure, and in that regard, the drawing figures should not be construed as limiting.

DETAILED DESCRIPTION

Figure 1:
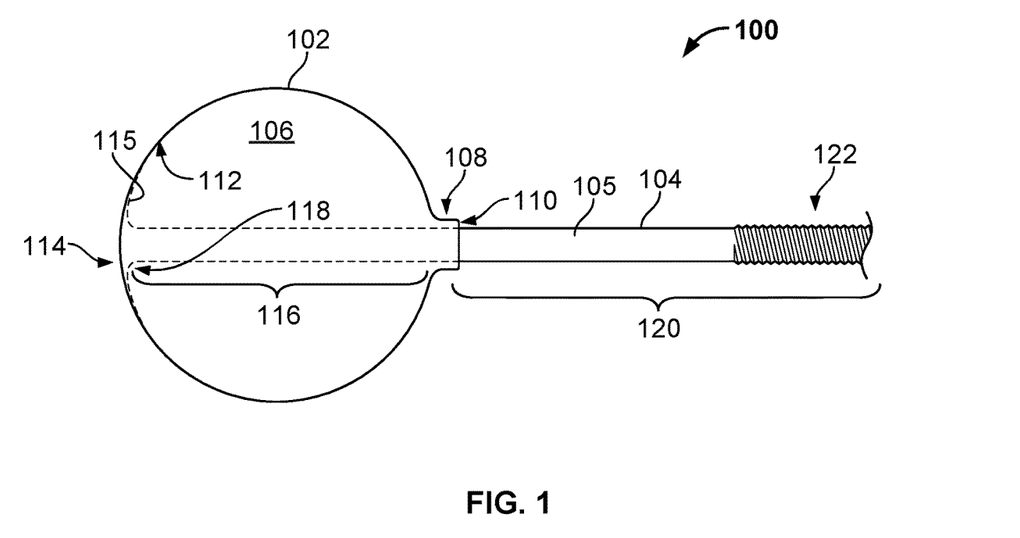
FIG. 1 is a side view of an example space-filling device that can be used to fill a cavity, a space, an intra-tissue site, an aperture, or a conduit within a body of a patient.

FIG. 1 illustrates an example space-filling device 100 that can be deployed within an organ, a cavity, an aperture, an intra-tissue site, a tissue void space, or a conduit within a patient. For example, in some implementations, the space-filling device 100 can be used to occupy a region within a stomach. In some examples, the space-filling device 100 can be used to occupy a cavity of a left atrial appendage (LAA) within a heart. In yet other examples, the space-filling device 100 can be used to occlude a body vessel, or to occupy a cavity of an aneurysm (e.g., a cerebral aneurysm or a cardiac aneurysm). In other instances, the space-filling device 100 can be used, for example, to occupy a region formed by a tumor bed, as an implant device (e.g., breast implants, facial implants, et al.), to fill a void left after a surgery or after shrinkage of a tumor, or used in a tamponade application to address a gaping wound, or used to expand an intra-tissue site. In some instances, the space-filling device 100 can be used, for example, to generate space between tissues or tissue layers. For example, in some embodiments the space-filling device 100 is used to develop a cavity or space in which to insert an implant (e.g. a breast implant, tissue filler, a pacemaker, or a sensor).

The space-filling device 100 can be delivered through or over a catheter system to a delivery site, such as the stomach or other appropriate delivery site. When delivered to the stomach, for example, the space-filling device 100 can subsequently be partially or completely filled such that the space-filling device 100 occupies a region of a body of the stomach. In some embodiments, the extent of filling of the balloon is directly visualized by the operator using, for example, an endoscope. In some embodiments, the extent of filling is monitored by tracking relative positions of one or more markers on or around the periphery of the balloon. In some embodiments, the extent of filling of the balloon is determined based on the amount of the one or more filling materials delivered to the lumen. As such, the body of the stomach may thereafter include a reduced amount of void space due to the presence of the space-filling device 100, which may reduce the appetite of the patient. In some examples, the space-filling device 100 may be removed or repositioned from the original delivery site, as will be described in further detail below. In some embodiments, the extent of filling of the balloon is directly visualized by the operator endoscopically using, for example, a camera. In some embodiments, the extent of filling is monitored by tracking relative positions of one or more markers on the balloon member or around the periphery of the balloon. In some embodiments, the extent of filling of the balloon is determined based on the amount of the one or more filling materials delivered to the lumen. In some embodiments, the clinician pre-plans the amount of the one or more filling materials delivered to the lumen based on one or more of patient weight, patient age, or patient condition.

As shown in FIG. 1, the space-filling device 100 includes a balloon member 102 or bag and a tubular member 104 that extends into the balloon member 102 from outside of the balloon member 102. The balloon member 102 defines an internal compartment 106 and includes a port 108 disposed at a proximal end 110 of the balloon member 102. The port 108 provides a point of access to the internal compartment 106 from an area exterior of the balloon member 102. Within the internal compartment 106, the tubular member 104 extends from an internal surface 112 of the balloon member 102 near a distal end 114 of the balloon member 102, and exits the internal compartment 106 via the port 108. As can be seen in FIG. 1, a first portion 116 of the tubular member 104 is disposed interior of the internal compartment 106, and a second portion 120 of the tubular member 104 is disposed exterior of the internal compartment 106.

As noted above, for illustrative purposes, a balloon member 102 is utilized to describe various embodiments herein although other vessel members are contemplated and described. Accordingly, while example space-filling device 100 includes a balloon member 102, in some embodiments, containment structures other than a balloon are used as vessel members. For example, in some such embodiments one or more coil frame structures that define an internal compartment space can be used. In some embodiments, multiple vessel members may be utilized. In some embodiments, one or more balloons are used in combination with one or more non-balloon expandable containment structures. For example, in some embodiments one or more coil frame structures that define an internal compartment space are used with one or more balloon members. Such vessel members, for example, a coil frame structure, can be expandable similar to the balloon member 102 described herein. In some embodiments, other suitable types of expandable containment structures can be used as vessel members, including, for example, polyurethane foam, silicone foam, shape memory foam, and swellable substances such as hydrogels.

A distal end 118 of the tubular member 104 may be attached to the internal surface 112 in any appropriate manner, such as with adhesive or other type of bond (e.g., various types of welds). In some embodiments, the tubular member 104 and balloon member 102 may be formed integrally, of the same material. In some examples, including the example shown in FIG. 1, the distal end 118 of the tubular member 104 includes a collar 115 or rim surface that can be secured to the internal surface 112 in any appropriate manner, such as with adhesive or other type of bond.

As can be seen in FIG. 1, the tubular member 104 extends out of the internal compartment 106 of the balloon member 102 through the port 108. The tubular member 104 defines a lumen 105 within the tubular member 104 that is adapted to receive one or more filling materials. The one or more filling materials are contained within the lumen 105 of the tubular member 104, and do not exit the lumen 105 at the distal end 118 of the tubular member 104 in embodiments wherein the lumen 105 is sealed at its distal end 118. In some embodiments, a portion of the internal surface 112 of the balloon member 102 seals the lumen 105 at the distal end 118 of the tubular member 104, based on the attachment of the distal end 118 and/or the collar 115 (for example in some embodiments that include a collar 115). In some implementations, the distal end 118 of the tubular member 104 is integral with the inner surface 112 of the balloon member 102, thereby sealing the lumen 105 at the distal end 118 of the tubular member 104. In some embodiments, the lumen 105 is sealed by another method that closes the lumen 105 at its distal end 118, such as a clip device, stitching, adhesive, welding, and the like. In this manner, filling material that is delivered into the lumen 105 of the tubular member 104 may be contained within the lumen 105 of the tubular member 104, and does not exit the lumen 105 of the tubular member 104. For example, filling material delivered into the lumen 105 may not be disposed within internal compartment 106 of the balloon member 102 outside of the lumen 105 of the tubular member 104.

The port 108 of the balloon member 102 may be sized to allow passage of the tubular member 104 through the port 108. In some implementations, the port 108 may include an elastic property. For example, a size of an opening defined by the port 108 may vary at least in part based on a pressure applied to walls of the port 108, and the walls of the port 108 (or a lip of the port 108) may provide a compression fit against the tubular member 104. For example, the pressure applied to the walls of the port 108 or the lip of the port 108 may be based on a volume or area occupied by a portion of the tubular member 104 that is circumferentially surrounded by the walls of the port 108 or the lip of the port 108, where the volume or area occupied by the tubular member 104 may be related to a delivery of filling material, as will be further described below. In some implementations, the compression fit may substantially or completely prevent ingress of bodily fluids to the internal compartment 106 of the balloon member 102. In some implementations, the port 108 may not include an elastic property, and may have a fixed diameter.

In some embodiments, a proximal end of the tubular member 104 may be configured so that it does not pass through the port 108, and remains exterior of the balloon member 102. A clinician may later remove the device 100 from the patient, for example by using an endoscope to view and grasp the proximal end of the tubular member 104 and withdraw the tubular member 104 from the balloon member 102, and withdraw the entire balloon member 102 that may become everted in the process. In some examples, such as examples where the device 100 is intended to permanently occlude a vessel or structure (e.g., LAA) the proximal end of the tubular member 104 may pass through the port 108 and enter the balloon member 102.

In some implementations (such as permanent implant applications), the port 108 may include a valve. For example, the port 108 may include a one-way valve that permits the tubular member 104 to enter the internal compartment 106 of the balloon member 102 and restricts the tubular member 104 from exiting the internal compartment 106. A typical duckbill-type valving system could be used in some implementations. The valve may be predisposed to be in the closed position, and increased internal pressure may contribute to its sealing efficiency.

The space-filling device 100 may be configured such that, when a filling material is delivered into the lumen 105 of the tubular member 104, one or more portions of the tubular member 104 that were exterior of the internal compartment 106 of the balloon member 102 prior to the delivery may be caused, upon delivery of the filling material, to enter the internal compartment 106 of the balloon member 102 through the port 108. The one or more portions of the tubular member 104 may be received into the internal compartment 106 of the balloon member 102, and may remain within the internal compartment 106 (see, e.g., FIG. 6).

In some implementations, the space-filling device 100 may assume various configurations. For example, the balloon member 102 may be relaxed, and the space-filling device 100 may assume a generally collapsed configuration (see FIG. 5), in which the balloon member 102 occupies a first volume when the lumen 105 of the tubular member 104 is generally empty. In some implementations, prior to delivering a filling material into the lumen 105, a minimal length of the tubular member 104 (such as distal portion 116 shown in FIG. 1) of the tubular member 104 may be disposed interior of the internal compartment 106.

The balloon member 102 may begin to expand and the space-filling device 100 may assume a partially filled configuration as a filling material is delivered into the lumen 105 of the tubular member 104. For example, the balloon member 102 may occupy a second volume when the lumen 105 of the tubular member 104 is at least partially filled with the filling material, or when a distal portion of the lumen 105 of the tubular member 104—corresponding to one or more partially-filled-portions of the tubular member 104—is substantially or completely filled with the filling material. In this example, a force associated with the delivery of the filling material may cause the partially filled portion of the tubular member (which may have been exterior of the internal compartment 106 prior to the delivery) to enter the internal compartment 106 of the balloon member 102 through the port 108. The second volume may be greater than the first volume. As additional filling material is delivered into the lumen 105 of the tubular member 104, a force associated with the delivery of the additional material may cause an additional length of the tubular member 104 (which had been exterior of the internal compartment 106 prior to the additional delivery) to enter the internal compartment 106 of the balloon member 102 through the port 108. In a fully deployed or space-occupying configuration for the space-filling device 100, the balloon member 102 may occupy a third volume that is larger than the first and second volumes. This may occur, for example, when a majority of the tubular member 104 is substantially or completely filled with the filling material and is located interior of the internal compartment 106 (having passed through the port 108), with a smaller portion of the tubular member 104 remaining exterior of the internal compartment 106 and outside of the port 108.

In some embodiments, the balloon member 102 may be configured to expand to a predetermined shape when the internal compartment 106 is partially or completely filled by the tubular member 104 and the filling material contained within the lumen 105 of the tubular member 104. In the example of FIG. 1, even though the interior compartment 106 is not substantially or completely filled by the tubular member 104, the balloon member 102 is shown in its expanded shape of a sphere for clarity. In practice, the balloon member 102 may assume a generally collapsed configuration in such a situation, as described above. Examples of predetermined shapes that the balloon member may be configured for can include a sphere, ellipsoid, other three-dimensional shape having generally rounded edges, a generally cube or box shape, a pyramid shape, a conical shape, or any other appropriate shape.

In some embodiments, the balloon member 102 may include a flat pattern welded between two pieces of anisotropic material (e.g., films) where, because of the orientation of the films, upon delivery of the filling material to the tubular member 104, the balloon member 102 may expand into a ball shape.

In some embodiments, the balloon member 102 may be non-distensible such that balloon member 102 may be partially or completely filled to achieve a maximum predetermined fixed size. In some embodiments, the balloon member 102 may be distensible such that the balloon member 102 can stretch to accommodate an additional portion of the tubular member 104 (as compared to a portion of tubular member 104 that would be accommodated by a non-distensible balloon member 102). In some implementations, the balloon member 102 may conform to a size of a cavity at the delivery site. In some implementations, the balloon member 102 may have a diameter of about 3 mm to about 50 mm, and in general, the diameter (or volume) may be selected according to a particular delivery site at which the space-filling device 100 will be deployed. For example, a space-filling device 100 selected for deployment in the stomach may include a balloon member 102 having a volume of about 300-500 $cm^3$, whereas a space-filling device 100 selected for deployment in the LAA may include a balloon member 102 having a volume of about 15 $cm^3$.

In some embodiments, filling the balloon member 102, such as when the one or more filling materials are delivered into the lumen 105 of the tubular member 104 or when tubular member 104 is advanced into the internal compartment 106 of the balloon member 102, for example, by a delivery catheter 124 (refer to FIG. 2), results in a change in volume. In some embodiments, the change in volume of the balloon member 102 is an increase in the volume. In some embodiments, filling the balloon member 102 does not result in a change in the volume of the balloon member 102 but instead results in a change in the buoyancy of the balloon member 102. In some embodiments, filling the balloon member 102 results in a change in the volume of the balloon member 102 as well as a change in the buoyancy of the balloon member 102.

In some implementations, an operator (e.g., a physician) may determine a final desired deployed size of the space-filling device 100, such as by determining how much filling material is to be delivered into the lumen 105 of the tubular member 104 and by determining an appropriate volume to be occupied by the balloon member 102. In some embodiments, one or more radiopaque markers are included at locations on the balloon member 102 to assist an operator in visualizing the deployed size and location of the space-filling device 100. In some embodiments, a contrast medium filling material, or a contrast medium additive, is used in the filling material to assist an operator in visualizing the deployed size and location of the space-filling device 100.

In some embodiments, the balloon member 102 may include one or more relatively stiff surface regions on an outer surface of the balloon member 102. The stiff surface region may be adapted to promote fluid flow past the stiff surface region. For example, a space-filling device 100 selected for implantation in the LAA may include a relatively stiff surface region that may be disposed across an ostium of the LAA to promote blood flow along the stiff surface region and past the LAA within a left atrial chamber. In some embodiments, the stiff surface region may surround the port 108 of the balloon member 102.

As shown in FIG. 1, the balloon member 102 initially (prior to the delivery of filling material) encloses a distal portion 116 of the tubular member 104 that may correspond to at least a width or diameter of the balloon member 102. For example, in the example where the balloon member 102 takes the shape of a sphere, the balloon member 102 may initially enclose a portion of the tubular member 104 that corresponds to a diameter of the sphere. In some examples, a larger or smaller portion of the tubular member 104 may initially be enclosed by the balloon member 102. As described above, the balloon member 102 may be sized to receive an additional portion of the tubular member 104 when the additional portion of the tubular member 104 is folded (e.g., jumbled) upon itself within the internal compartment 106 of the balloon member 102 (see FIG. 6), such as when the one or more filling materials are delivered into the lumen 105 of the tubular member 104, or when tubular member 104 is advanced into the internal compartment 106 of the balloon member 102, for example, by a delivery catheter 124.

In some embodiments, the balloon member 102 is impermeable to fluids that may surround or contact the space-filling device 100 at the delivery site. In some embodiments, the balloon member 102 is permeable or semipermeable to one or more fluids that may surround or contact the space-filling device 100 at the delivery site. In some embodiments, the tubular member 104 may be permeable or semipermeable and may permit at least a portion of the filling material to escape from the lumen 105 of the tubular member 104, which filling material may then pass through the permeable or semipermeable balloon member 102 (or membrane, discussed below).

In some embodiments, the space-filling device 100 may include a membrane (not shown) that generally surrounds the balloon member 102 and that is permeable or semipermeable to fluids that may surround or contact the space-filling device 100 at the delivery site. In some examples, a region between the balloon member 102 and the membrane may include one or more therapeutic substances having particles that are sized appropriately so as to be able to diffuse or move through pores within the balloon membrane and that are targeted for certain molecules near the delivery site. For example, a space-filling device 100 selected for implantation in the stomach may include one or more substances that treats and/or soothes an upset stomach condition. In another example, a space-filling device 100 selected for implantation in the LAA may include a substance that initiates a biological response to promote rapid ingrowth. In some examples, the pores within the membrane may permit tissue ingrowth into the balloon member 102 at the delivery site, to help secure at least a portion of the outer surface of the space-filling device 100 to tissue at or surrounding the delivery site. In some embodiments, the outer surface of the space-filling device comprises a polytetrafluoroethylene (PTFE) or expanded PTFE (ePTFE) laminate.

As used herein, the term "therapeutic substance" includes substances which modulate a biological or physiological process. For example, in some embodiments, a space-filling device 100 selected for implantation in the stomach treats and/or relieves gastric distress or symptoms of gastric distress. In some embodiments, a space-filling device 100 selected for implantation in the LAA may include one or more therapeutic substances that initiate or increase a biological response to promote rapid ingrowth of tissue in or around the space-filling device 100 and/or one or more anchors disposed on the balloon 102 of the space-filling device 100.

As used herein, "therapeutic substances" include, without limitation, Analgesics; Anti-coagulants; Anti-inflammatory agents; Anti-infective agents; Anti-mitotic agents; Anti-platelet agents; Anti-thrombolytic agents; Anti-thrombogenic agents; Hyperplastic agents; Procoagulants; Antacids; Anti-acid reflux agents; Thrombolytic agents; Thrombogenic agents; Vascular Sclerosants; Claudication agents; Serotonergic agents; Vasodilators/Antihypertensives; Vasoconstrictors; Antihyperplastic/cytotoxic agents; Immunosuppressants; Antidysrhythmic agents; Local Anesthetics; Cholesterol Lowering agents; Growth factors; and steroids. Examples of therapeutic substances include, but are not limited to, heparin, sirolimus, paclitaxel, everolimus, ABT-578, dexamethasone, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, thalidomide, unfractionated Heparin Sulfate Enoxaparin (Lovenox) MW 4500, Dalteparin (Fragmin), Tinzaparin (Innohep), Bemiparin, Certoparin, Nadroparin, Parnaparin, Reviparin, Fondaparinux (Arixtra), Danaparoid (Orgaran), Coumadin (Warfarin), Acenocoumarol, Phenprocoumon, Rivaroxaban (e.g. Apixaban), Hirudin (e.g. Lepirudin (Refludan), Bivalirudin (Angiomax), Argatroban (Novastan), Dabigatran (Pradaxa)), Ancrod (Viprinex), and Batroxobin (e.g. Hementin), Ranitidine, Pantoprazole, Dexlansoprazole, Esomeprazole, Lansoprazole, Famotidine, Propantheline, Rabeprazole, Almacone, Nizatidine, Simethicone, Mepenzolate, Methscopolamine, Metoclopramide, Cimetidine, among others.

The balloon member 102 can be formed of one or more of a variety of biocompatible materials, such as PTFE, ePTFE, silicone, or an elastomeric fluoropolymer, such as described in one or more of U.S. Pat. Nos. 7,049,380, 7,462,675, and 8,048,440, the contents of which are each incorporated by reference herein. In implementations that include a membrane, the membrane can be formed of one or more of a variety of biocompatible materials, such as PTFE, ePTFE, or silicone. In some embodiments, an external surface of the balloon member 102 (or membrane, if so equipped) includes a material that prevents or reduces a chance that the balloon member 102 adheres to cells or tissue at the delivery site, such as in implementations where it is desired that the device 100 remain generally not adhered to its surroundings (within a stomach, for example).

As described above, in some embodiments, the distal end 118 of the tubular member 104 may be secured or attached to the internal surface 112 of the balloon member 102 with a biocompatible adhesive substance, such as fluorinated ethylene propylene (FEP). The biocompatible adhesive substance may similarly be used to affix a collar 115 of the tubular member 104 to the internal surface 112 of the balloon member 102 for embodiments of the tubular member that include a collar 115. In other embodiments, the distal end 118 of the tubular member 104 may be integral to the internal surface 112 of the balloon member 102. In some embodiments, the distal end 118 of the tubular member 104 may be removably attached to the internal surface 112 of the balloon member 102.

A width of the tubular member 104 can be sized to pass through the port 108 of the balloon member 102. A length of the tubular member 104 can be sized to provide a desired volume for the balloon member 102 when the space-filling device 100 assumes a fully deployed configuration. This may occur, for example, when a predetermined amount of filling material has been delivered into the lumen 105 of the tubular member 104, when a sufficient amount of the filling material has been delivered to cause a desired length of the tubular member 104 to pass through the port 108 and into the internal compartment 106 of the balloon member 102, or when the balloon member 102 occupies a desired volume or adequately occupies a cavity or void region at a delivery site.

Prior to delivering a filling material into the tubular member 104, a portion 120 of the tubular member 104 extends external to the balloon member 102 (i.e., proximal to the port 108), as can be seen with reference to FIG. 1. In a general embodiment, the length of the portion 120 of the tubular member 104 may depend on the volume of the balloon member 102. Either or both of an inner diameter and an outer diameter of the tubular member 104 may be sized such that the tubular member 104 can engage a distal end of a delivery catheter 124 (see FIG. 2). In some examples, a portion of the tubular member 104 may include an attachment feature designed to engage a delivery catheter (e.g., a keyed feature).

The structure of the space-filling device 100 provides the space-filling device 100 with a relatively low profile, which may substantially prevent or reduce the extent to which the space-filling device 100 may potentially cause an obstruction near the delivery site at which the space-filling device 100 is deployed, as compared to potential obstructions caused by alternative space-filling devices. For example, in some embodiments the space-filling device 100 may be assembled in situ, in contrast to many other space-filling devices that may be delivered in whole wherein their entire mass is compressed and passed through a delivery system. The low profile of the space-filling device 100 may further provide for easy removal of the space-filling device 100 from the delivery site, as the device 100 may similarly be disassembled in situ, and then removed.

Filling material can be delivered into the lumen 105 of the tubular member 104 to cause the space-filling device 100 to expand. As used herein, the terms "delivered", "deliver", or "delivering" (or other variations of the terms) are meant to include, without limitation, filling, conveying, administering, adding, infusing, introducing, or otherwise providing material into the lumen 105 in any suitable manner.

Figure 2:
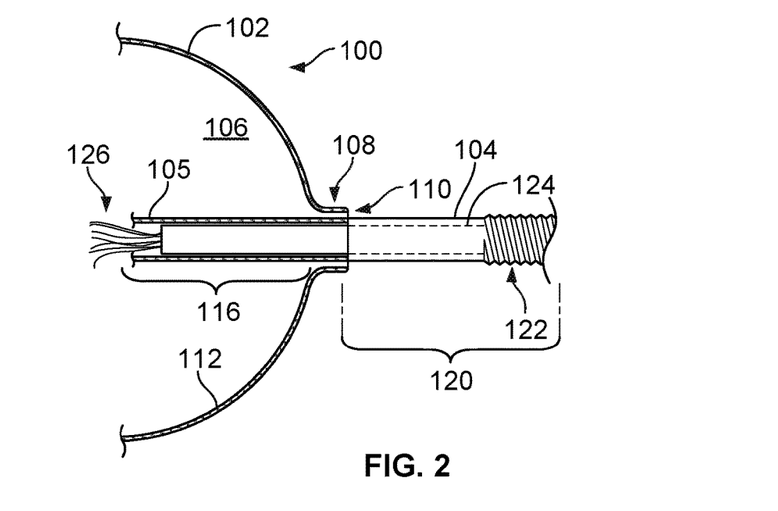
FIG. 2 is an enlarged side view of a portion of the space-filling device of FIG. 1 as coupled with an example delivery catheter.

FIG. 2 illustrates an enlarged view of the tubular member 104 and the proximal end 110 of the balloon member 102, as coupled with a delivery catheter 124. In some embodiments, the tubular member 104 can be sized so that the delivery catheter 124 can be freely inserted within the lumen 105 of the tubular member 104 (e.g., by having an inner diameter of the tubular member 104 slightly larger than an outer diameter of the delivery catheter 124), where the tubular member 104 may generally not provide an appreciable amount of compressive force to an exterior surface of the delivery catheter 124. In some embodiments, the tubular member 104 can be sized to have an inner diameter slightly smaller than an outer diameter of the delivery catheter 124, where the tubular member 104 may generally provide a small amount of compressive force to the exterior surface of the delivery catheter 124. In some implementations, the tubular member 104 may have an elasticity that permits the tubular member 104 to stretch around and thereby grasp the delivery catheter 124. In some embodiments, a wall of a proximal region 122 of the tubular member 104 may include a portion of gathered material (e.g., wrinkled, creased, or scrunched) that may improve the engagement of the proximal region 122 of the tubular member 104 with the delivery catheter 124. The embodiments with the portion of gathered material may also allow for additional lengths of the tubular member 104 to be loaded onto the delivery catheter 124, so that a tubular member 104 that is longer or much longer than the length of the delivery catheter 124 on which it is mounted may be delivered. For example, for a delivery system that includes a delivery catheter 124 with length of 100 cm, with a tubular member 104 of length, for example, about 150-300 cm or more may be loaded onto the delivery catheter 124, where a proximal portion 122 of the material of tubular member 104 is gathered.

In some implementations, the delivery catheter 124 may be inserted into the lumen 105 of the tubular member 104, and may be advanced through the port 108. As will be described in more detail below, a filling material 126 may be delivered through the delivery catheter 124 and into the lumen 105 of the tubular member 104. A force imparted by the filling material 126 to the walls of the lumen 105 may cause one or more portions of the tubular member 104 to be advanced through the port 108 and into the interior compartment 106 of the balloon member 102. For example, the filling material 126, after exiting the distal end of the delivery catheter 124, may pass into and through the lumen 105 of the tubular member 104. Some of the filling material 126 may impart a distally-directed or transversely directed hydraulic force on an interior wall of the tubular member 104, which may encourage one or more portions of the tubular member 104 to enter the interior compartment 106 through the port 108 as the lumen 105 of the tubular member 104 is being filled with the filling material 126. Some of the filling material 126 may impart a distally-directed hydraulic force on the portion of the internal surface 112 of the balloon member 102 that seals the distal end 118 of the tubular member, and upon encountering the internal surface 112 (or upon encountering filling material 126 already within the lumen 105, having been earlier delivered or predisposed), may rebound or deflect and impart a hydraulic force to the interior wall of the tubular member 104, which may encourage the tubular member 104 to enter the interior compartment 106 through the port 108 as the lumen 105 of the tubular member 104 is being filled with the filling material 126. In some examples, the interior surface of the tubular member 104 may include fins, cupped sections, or features that provide resistance to the delivered filling material 126, and help to transmit a force from the filling material 126 to the walls of the lumen 105 as the filling material 126 is injected, which force may thrust the tubular member 104 into the internal compartment 106 of the balloon member 102.

One or more portions of the tubular member 104 may tumble upon itself within the interior compartment 106, and may occupy space within the interior compartment 106. An exterior surface of the tubular member 104 may impart a force to the interior surface 112 of the balloon member 102, and may cause the balloon member 102 to expand from an initial collapsed configuration as additional portions or additional lengths of the tubular member 104 pass through the port 108 and into the interior compartment 106 as filling material 126 is delivered into the lumen 105 of the tubular member 104. As described above, the delivered filling material 126 may be contained within the lumen 105 of the tubular member 104, and may not exit the lumen 105 of the tubular member 104. For example, in some embodiments, no portion of the delivered filling material 126 may exit the tubular member 104. For example, the delivered filling material 126 may be contained within the lumen 105 of the tubular member 104, and may be restricted from exiting the lumen 105 of the tubular member 104 at the distal end 118 by the seal provided by the portion of the inner surface 112 of the balloon member 102, and may be restricted at the proximal end by the stopping member or clamping member, discussed above.

In some implementations, the delivery catheter 124 is held in place throughout the delivery of the filling material 126. In some examples, an initial portion of the filling material 126 may be delivered with the delivery catheter 124 at a first position (e.g., with a distal end of the delivery catheter 124 disposed within the internal compartment 106 of the balloon member 102, as shown in FIG. 2), and one or more subsequent portions of the filling material 126 may be delivered with the delivery catheter 124 at a second position, (e.g., with a distal end of the delivery catheter disposed exterior of the internal compartment 106 of the balloon member 102). In some examples, the distal end of the delivery catheter 124 may not pass through the port 108 when delivering the filling material 126, and the filling material 126 may be delivered from a location outside of the internal compartment 106. For example, filling materials 126 may be delivered at first, second and third positions (e.g., with a distal end of the delivery catheter 124 disposed within the internal compartment 106 of the balloon member 102; with a distal end of the delivery catheter 124 disposed at an interface of the exterior and the interior of the internal compartment 106 of the balloon member 102; and with a distal end of the delivery catheter 124 disposed exterior of the internal compartment 106 of the balloon member 102).

In some implementations, a proximal end of the tubular member 104 is further adapted to be closed-off or capped following removal of the delivery catheter 124 from the tubular member 104, to restrict or prevent ingress or egress of fluid or material to the lumen 105 of the tubular member 104. In some embodiments, the space-filling device 100 may include a stopping member (e.g., a cap (not shown)) that can be inserted into the proximal end of the tubular member 104 following removal of the delivery catheter 124. Alternatively, a clamping member may be clamped onto the proximal end of the tubular member 104. In some embodiments, the stopping member or clamping member may be made of one or more biocompatible materials such as silicone or elastomeric fluoropolymer, for example as described in U.S. Pat. Nos. 8,048,440, 7,462,675, and 7,049,380, the contents of which are herein incorporated by reference in their entirety. In some embodiments, the proximal region 122 of the tubular member 104 may be formed of a self-sealing material that can seal itself upon being removed from the delivery catheter 124. For example, for materials having very low viscosity (e.g., some foams or gels), a seal of the proximal end of the tubular member may not be used.

In some embodiments, the stopping member or clamping member may be sized to prevent the proximal end of the tubular member 104 from passing through the port 108. For example, the stopping member or clamping member may have a width (e.g., a diameter) that is larger than a diameter of an opening of the port 108. In the case of the stopping member (e.g., a cap), the proximal end portion of the tubular member 104 may stretch to accommodate the stopping member, so that when the stopping member is located at the proximal end of the tubular member 104, the proximal portion of the tubular member may not pass through the port 108 and remains exterior of the internal compartment 106. In some examples, the proximal end portion of the tubular member 104 may be flared outward so that at least a portion of the proximal end portion of the tubular member 104 is sized to avoid passing through the port 108. For example, a width (e.g., diameter) of the flared portion of the tubular member 104 may exceed a diameter of the opening of the port 108. A clip may be used to seal the proximal end of the tubular member 104. For example, a circular NiTi clip may clamp the proximal end of the tubular member 104 shut and prevent the proximal end of the tubular member 104 from entering the balloon member 102.

The lumen 105 of the tubular member 104 is adapted to receive one or more deliveries of one or more filling materials 126. The tubular member 104 can be made of a material that is sufficiently elastic, flexible, conformable, and compliant such that the tubular member 104 can be thrust along the distal end of the delivery catheter 124 and into the internal compartment 106 of the balloon member 102 as a filling material 126 is delivered into the lumen 105 of the tubular member 104 via the delivery catheter 124. As the tubular member 104 is thrust into the internal compartment 106 of the balloon member 102, the elasticity, flexibility, conformability, and compliance of the tubular member 104 allows the tubular member 104 to fold (e.g., jumble) upon itself to randomly pack and at least partially fill within the internal compartment 106 of the balloon member 102 (see FIG. 6). In some implementations, the tubular member 104 and filling material 126 contained within the tubular member 104 substantially fill or completely fill the internal compartment 106 of the balloon member 102.

The tubular member 104 may further be constructed of a material that has a tensile strength sufficient to allow the tubular member 104 to be removed (e.g., pulled) by providing a withdrawal (e.g., proximally directed) force at or near the proximal region 122 of the tubular member 104. The withdrawal force may be directed, for example, away from the delivery site without tearing, necking, or otherwise mechanically failing. In some embodiments, the tubular member 104 may be non-distensible such that the tubular member 104 may be filled with up to a maximum, predetermined fixed volume of the filling material 126.

In some embodiments, the tubular member 104 may be distensible such that the tubular member 104 can stretch to accommodate an additional volume of the filling material 126 (as compared to the volume that would be accommodated by a non-distensible tubular member 104). The tubular member 104 can be formed of one or more of a variety of biocompatible materials, such as PTFE, ePTFE, elastomers, or others. The tubular member 104 can be formed of one or more materials that are compatible with the one or more filling materials 126.

In some embodiments, the filling material 126 can include two or more substances. In some embodiments, the filling material 126 reacts with, combines with, or interacts with one or more materials included in the device 100 prior to delivery of the filling material 126. For example, an inner surface of the wall of the tubular member 104 may be pre-imbibed with a first filler substance 126 of a two-part filler system. The tubular member 104 may be pre-imbibed with a first reagent, and the delivery catheter 124 may be used to deliver a filling material that comprises a second reagent. In some examples, the second reagent may be functional to activate the first reagent. In some examples, a first filling material may be delivered by the delivery catheter 124, and then a second filling material may be delivered by the delivery catheter 124. The second filling material may activate the first filling material, in some examples. For example, the first filling material may be a calcium-containing solution, and the second material may be an alginate-containing solution. The alginate-containing solution may react with the calcium-containing solution, and they may expand.

In some examples, the first and second filling materials may differ in physical phase type. For example, the first filling material may be one of a solid, liquid, or gas (or other type), and the second filling material may be a different one of a solid, liquid or gas (or other type) as compared to the first filling material. In some examples, the filling material comprises at least one of a bioinert material and a biocompatible material.

The filling material 126 may include biocompatible liquids, solids, foams, gels, and gases. In some examples, the filling material 126 may be a radiopaque liquid. In some embodiments, the filling material 126 may be a saline solution. In some embodiments, the filling material 126 may include gels and/or foams. As defined herein, the term "gel" refers to any multi-part biocompatible substance that can be activated in situ or be caused to swell or increase in viscosity. As defined herein, the term "foam" refers to any substance that includes entrapped regions of gas. Open-cell foams may be used, for example. An open-cell polyurethane (PU) foam may be used. In some examples, the filling material 126 may be a silicone gel. In some embodiments, the filling material 126 may be a polyurethane gel. In some embodiments, the filling material 126 may be a solid material. For example, in some such embodiments the solid filling material 126 may be a granular solid material, a string-like solid material, or a super-elastic wire material.

In some embodiments, the tubular member 104 may be porous or micro-porous. In some examples where the tubular member 104 and the balloon member 102 are porous, the filling material 126 may include a therapeutic substance that can diffuse out of the space-filling device 100 through pores of the tubular member 104, the balloon member 102, and the membrane (if so equipped).

In some embodiments, the tubular member 104 or portions thereof may generally assume a random orientation within the internal compartment 106 of the balloon member 102 as the tubular member 104 is thrust off the delivery catheter 124 when the filling material 126 is delivered. In some embodiments, the tubular member 104 may include one or more features that facilitate an ordered packing of the internal compartment 106 of the balloon member 102 when the filling material 126 is delivered. For example, the tubular member 104 may be scored or segmented to have particular areas that are more likely to fold as the filling material 126 is delivered, and in this manner the internal compartment 106 of the balloon member 102 may be packed in a non-random manner or in a predetermined manner. In some examples, portions of the tubular member 104 may have a reduced thickness, for example, so that the tubular member 104 is more flexible in such areas, and where such areas are more conducive to folding versus other areas of the tubular member 104.

Figure 3:
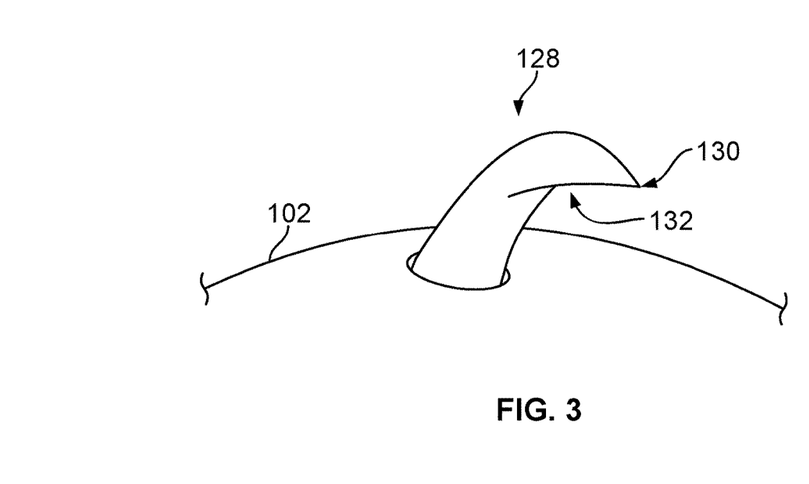
FIG. 3 is a perspective view of an example anchoring member extending from a balloon member of a space-filling device.

Referring now to FIG. 3, one or more anchoring members 128 may be distributed across an external surface of the balloon member 102 (or of the membrane, if so equipped) to promote permanent or temporary fixation of the space-filling device 100 to tissue at the delivery site. In some embodiments, the anchoring member 128 is formed to pierce tissue in a manner that secures the balloon member 102 of the space-filling device 100 to the delivery site. In some embodiments, the anchoring member 128 may be a barb or a hook. In some examples, the anchoring member 128 can be biodegradable or bioabsorbable, and thus may be resorbed over a period of time. In some examples, the bioabsorbable nature of the anchoring member 128 may promote acute fixation of the space-filling device 100 to tissue, facilitate tissue ingrowth, and reduce the risk of undesired tissue perforation. In some examples, the anchoring member 128 may terminate at a sharp point 130. In some embodiments, the anchoring member 128 may terminate at an atraumatic ball. In some embodiments, the anchoring member 128 includes a bend 132 along a length of the anchoring member 128. The bend radius may be about 0.06" to about 0.2." In various implementations, any appropriate number of anchoring members 128 may be included (e.g., zero, one, two, three, four, five, or six or more). In some embodiments, the space-filling device 100 does not include anchoring members 128 (e.g., for some implementations of the device 100 targeted for the stomach).

In some embodiments, the anchoring member 128 may be compliant, non-compliant, or partially compliant. In some embodiments, one or more portions or the entire surface of each of one or more anchoring members 128 may be coated with one or more biocompatible materials, such as a fluoropolymer (e.g., ePTFE or PTFE), polyester, a silicone, a urethane, or another suitable biocompatible material. In some embodiments, coated portions of the anchoring members 128 may provide a substrate that promotes tissue ingrowth at or around the anchoring members 128. In some embodiments, the coated portions of the anchoring members 128 may substantially prevent tangling of the anchoring members 128 with one another while the balloon member 102 is collapsed about the portion 116 (refer to FIGS. 1 and 2) of the tubular member 104 (e.g., when the balloon member 102 is not filled to its capacity). In some examples, the covered portion of the anchoring members 128 may limit an extent to which the anchoring members 128 can penetrate a tissue. In some embodiments, the coated portions of the anchoring members 128 may be impregnated with one or more therapeutic substances that are released in situ to elicit a desired biological or physiological response. For example, in some embodiments, one or more portions of the anchoring members 128 may be coated with a hyperplastic agent to promote tissue growth around the anchoring member 128. In some embodiments, the coated portions of the anchoring members 128 may provide texture that aids in securing the space-filling device 100 to the surrounding tissue at the delivery site.

In some implementations, the anchoring member 128 may be designed for atraumatic securing of the space-filling device 100 at the delivery site. For example, the anchoring member 129 may include a loop or a bend feature that may be used to secure the device 100 at the delivery site without puncturing tissue at the site.

In some implementations, an outside surface of the tubular member 104 may include bumps, stipples, ridges, points, or similar features. In some implementations, when the tubular member 104 is filled with the filling material and caused to occupy the internal compartment 106, these bumps, points, or topographies could imprint through the balloon member 102 material and cause an exterior surface of the balloon member 102 to become roughened. Such a roughened exterior surface of the device 100 may help to impede undesired migration of the device 100.

In some embodiments, the affinity for migration of the space-filling device 100 can be modulated by the addition of surface coatings on the exterior surface of the balloon member 102. For example, in some embodiments one or more portions of an exterior surface of the balloon member 102 is roughened or has an enhanced-frictional surface coating to impede undesired migration of the space-filling device 100. While in some embodiments the material of the balloon member 102 is initially constructed so as to have a roughened or enhanced-frictional surface, in some embodiments, the balloon 102 is treated or modified post-production to provide the roughened or enhanced-frictional surface. Conversely or additionally, in some embodiments, one or more portions of an exterior surface of the balloon member 102 is smoothened or includes a reduced-frictional surface coating to facilitate potential movement of the space-filling device 100 in relation to its surroundings. While in some embodiments the material of the balloon member 102 is initially constructed so as to have a smoothened or reduced-frictional surface, in some embodiments, the balloon 102 is treated or modified post-production to provide the smoothened or reduced-frictional surface.

Figure 4:
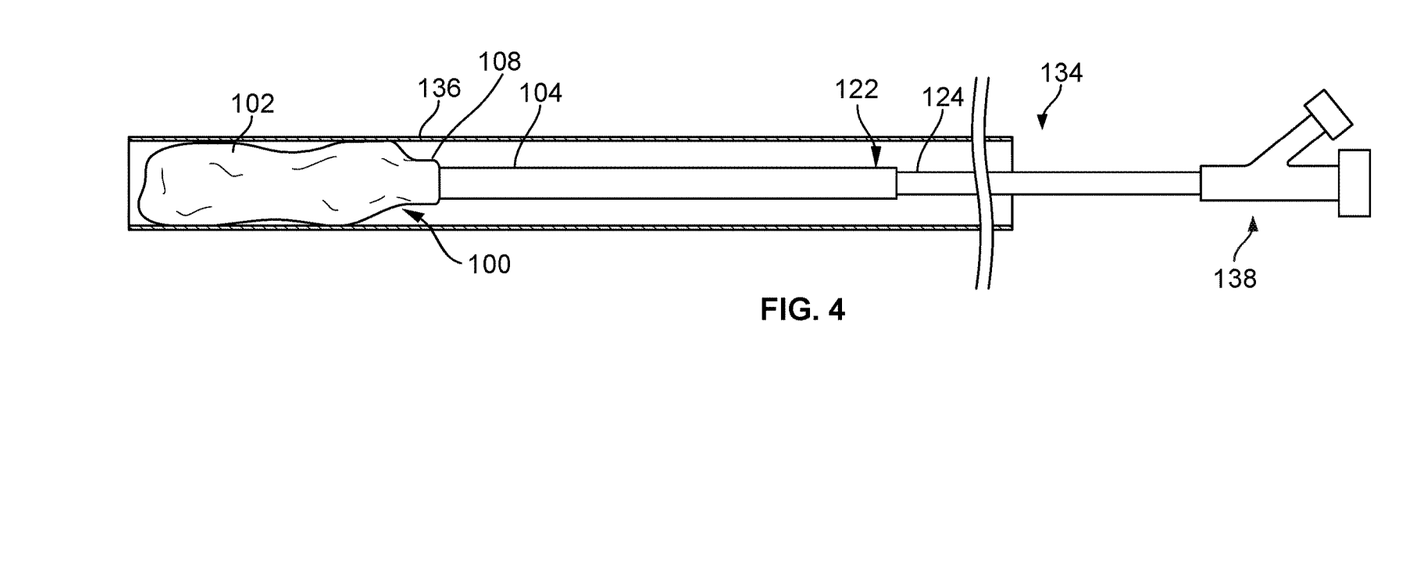
FIG. 4 is a side view of the space-filling device of FIG. 1 as coupled with an example delivery catheter system.

Referring to FIG. 4, the space-filling device 100 can be delivered to the delivery site using a catheter system 134. The catheter system 134 includes a delivery sheath 136, the delivery catheter 124, which may be positioned concentrically within the delivery sheath 136, and a pressurized delivery apparatus (not shown) that is adapted to deliver the filling material 126 to the delivery catheter 124. The catheter system 134 includes a delivery port 138 at its proximal end. The space-filling device 100 can be loaded on the delivery catheter 124 by initially engaging the distal end of the delivery catheter 124 with the proximal region 122 of the tubular member 104 (see FIG. 2). In some examples, the distal end of the delivery catheter 124 may be inserted into the proximal region 122 of the tubular member 104 and then further slid into the tubular member 104 (see FIG. 5). The delivery catheter 124 may typically be inserted slightly (e.g., about ⅓ of the balloon diameter) beyond the port 108 and within the internal compartment 106 of the balloon member 102. In other examples, the proximal region 122 of the tubular member 104 may be inserted into the distal end of the delivery catheter 124. Coupled with the delivery catheter 124, the space-filling device 100 is then forced through the delivery sheath 136 until the space-filling device 100 is positioned completely within the delivery sheath 136. In the example shown in FIG. 4, the tubular member 104 is wholly contained within the delivery sheath 136. In some examples, a portion of the tubular member 104 may extend beyond the delivery sheath 136 at the proximal end of the sheath 136.

When the space-filling device 100 is loaded within the delivery sheath 136, the delivery sheath 136 may be delivered to the delivery site in a manner as would be known to those skilled in the art. For example, the space-filling device 100 may be delivered to the LAA in an endovascular fashion. Ultrasound or fluoroscopic guidance may be used to assist with the delivery in some examples. An endoscope may be used. In some examples, the space-filling device 100 may be delivered to the stomach in a transesphogeal procedure and visualized directly via an endoscope. When a distal end of the delivery sheath 136 reaches the delivery site, the delivery catheter 124 may be pushed out of the delivery sheath 136 until the space-filling device 100 is positioned distal to the delivery sheath 136. In some instances, the delivery catheter 124 may be manipulated to position the balloon member 102 such that (e.g., for an embodiment of the space-filling device 100 that includes one or more anchoring members 128) the anchoring members 128 pierce tissue at the delivery site to secure the balloon member 102 at the delivery site. In some examples, one or both of the delivery catheter 124 and/or the delivery sheath 136 may be coated with a lubricant to facilitate delivery of the tubular member 104 over the delivery catheter 124, for example, or delivery of the space-filling device 100 out of the delivery sheath 136.

In some examples, the space-filling device 100 may include one or more radiopaque bands or radiopaque markers on one or more portions of the device 100 to aid in placement or positioning of the device 100 at the delivery site. For example, the device 100 may include a radiopaque marker near a distal end of the device (e.g., at or near the location where the distal end of the tubular member 104 attaches to the balloon member 102), and may additionally or alternatively include a radiopaque marker near a proximal end of the device (e.g., at or near the port 108). In some implementations, the delivery catheter 124 or delivery sheath 136 may include one or more radiopaque bands or radiopaque markers, and combinations of the above are possible.

Figure 5:
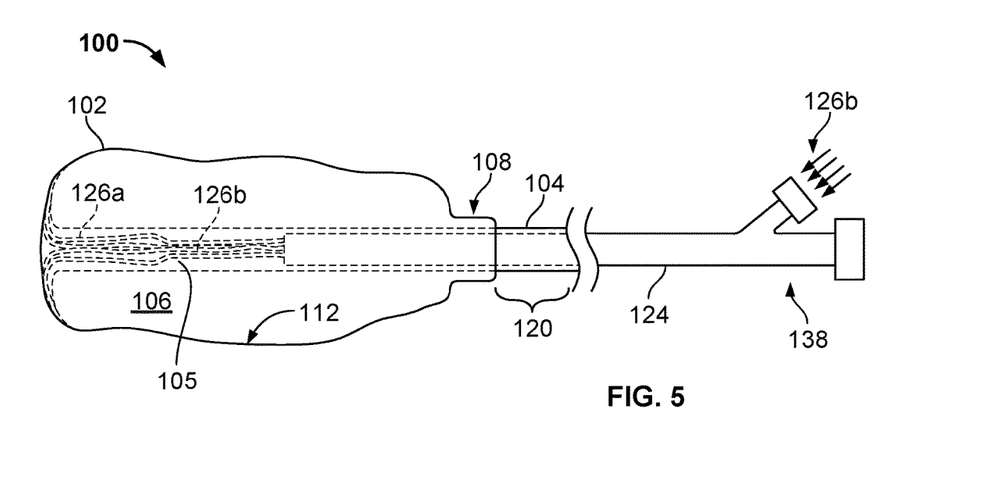
FIG. 5 is a side view of the space-filling device of FIG. 1 receiving an example filling material via the delivery catheter system of FIG. 4.

Referring to FIG. 5, an example of using two filling materials is described. An inner surface of the wall of the tubular member 104 is pre-imbibed with a first filling material or substance 126a. A second filling material 126b is delivered into the delivery port 138 of the delivery catheter 124. The delivered second filling material 126b interacts with the first filling material 126a, and activates the first filling material 126a (e.g., causing one or both of the first filling material 126a and the second filling material 126b to swell). As the second filling material 126b flows within the tubular member 104, a hydraulic force applied by the second filling material 126b to the tubular member 104 drives the tubular member 104 distally and causes a portion of the external portion 120 of the tubular member 104 to be pulled through the port 108 and into the internal compartment 106 of the balloon member 102. Additionally, the reaction of the first and second reagents 126a and 126b, and the resulting expansion (if appropriate) of the compound imparts additional force on the walls of the lumen 105 of the tubular member 104, which additionally pushes the tubular member 104 to jumble within the compartment 106, thereby pulling one or more portions of the tubular member 120 proximal of the port 108 into the compartment 106. In some examples, the tubular member 104 may not be pre-imbibed with a first filling material 126a. In such examples, the first filling material 126a is delivered to the lumen 105 of the tubular member 104 followed by subsequent delivery to the lumen 105 of the second filling material 126b. In some embodiments, the first filling material 126a interacts with and activates the second filling material 126b. In some embodiments, more than two filling materials are delivered, and two or more filling materials interact with and activate other filling materials. In some embodiments delivery of the one or more filling materials may be simultaneous.

In some implementations, buoyancy of the space-filling device 100 may be set or adjusted based on a delivered filling material 126. For example, the device 100 may be deployed for a period of time (e.g., a few hours, one day, several days, a week, or more), and thereafter it may be determined that an adjustment in buoyancy is desirable. For example, a buoyancy of the space-filling device 100 may be increased by delivering a first filling material 126, or may be decreased by delivering a second filling material 126. In some instances, delivering a liquid or gel filling material 126 to the lumen 105 of the tubular member 104 may decrease a buoyancy of the space-filling device 100. In some instances, delivering a gas filling material 126 to the lumen 105 of the tubular member 104 may increase a buoyancy of the space-filling device 100. In examples where a PU foam is used as a filling material, a further delivery of saline may be used to adjust buoyancy of the device 100. The saline may fill pores in the foam, for example, and may reduce the buoyancy of the device 100. With some implementations, including some implementations of the space-filling device 100 targeted for a stomach application, providing such adjustability to buoyancy may provide advantages, including increased patient comfort. For example, satiety sensors are located near the top of the stomach, near the cardiac sphincter, and a space-filling device 100 that floats on top of stomach contents may suppress hunger signals sooner than a device 100 that does not float.

Figure 6:
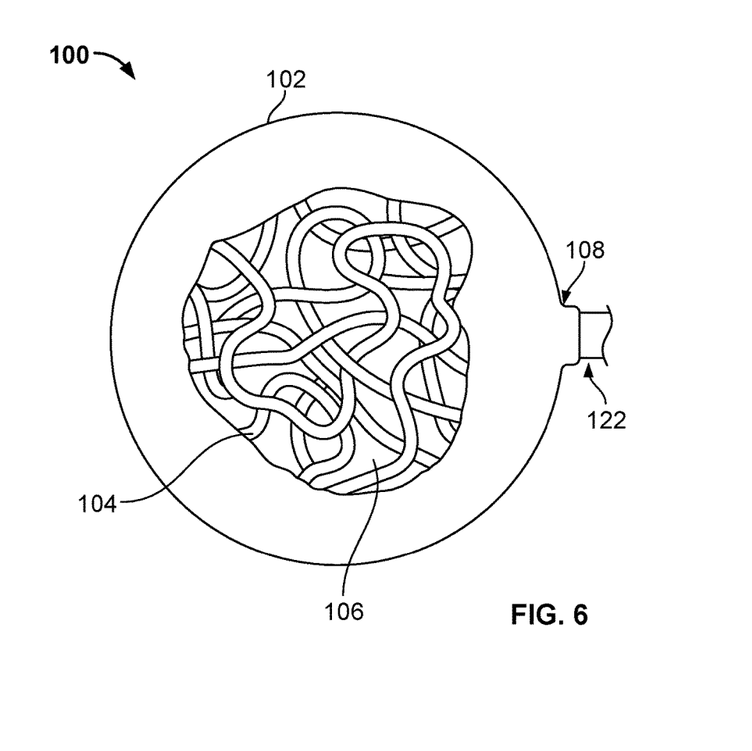
FIG. 6 is a side cutaway view of the space-filling device of FIG. 1 after receiving the filling material.

Whether a single filling material 126 (e.g., as described above with reference to FIG. 2), or two or more filling materials 126a and 126b (e.g., as described above with reference to FIG. 5) are used, as the one or more portions of the tubular member 104 is forced into the internal compartment 106, the one or more portions of tubular member 104 may fold (e.g., jumble) upon itself to pack and fit within the internal compartment 106 of the balloon member 102. As the one or more portions of the tubular member 104 packs into the internal compartment 106 of the balloon member 102, the balloon member 102 may conform to accommodate the one or more portions of the tubular member 104. In various implementations, the balloon member 102 may take on a prescribed shape (e.g., a spherical shape as shown in FIG. 6), or may take on a shape of a cavity in which it is disposed at the delivery site. FIG. 6 shows a side cutaway view of an example device 100 with one or more portions of the tubular member 104 that is tumbled, jumbled, or randomly packed within the internal compartment 106 of the balloon member 102. In some implementations, the one or more portions of tubular member 104 may be packed more densely than shown in FIG. 6, for example.

The lumen 105 of the tubular member 104 may be filled with a sufficient quantity of the filling material 126 until one or more portions of the tubular member 104 is disposed substantially within the internal compartment 106 of the balloon member 102 (e.g., where only a relatively small portion of the proximal region 122 of the tubular member 104 remains external to the port 108 of the balloon member 102, as illustrated in FIG. 6). As a result of at least a portion of the proximal region 122 of the tubular member 104 remaining external to the port 108 of the balloon member 102, and because the distal end 118 (refer to FIG. 1) of the tubular member 104 is sealed to the inside surface 112 of the balloon member 102, the tubular member 104 may be prevented from knotting upon itself or kinking within the internal compartment 106 of the balloon member 102. In some implementations, this feature can prevent obstructions from forming (e.g., kinks in the tubular member 104) so that a desired amount of filling material 126 may be injected. In some implementations, avoiding knotting of the tubular member 104 within the internal compartment 106 may facilitate later withdrawal of the tubular member 104 from the internal compartment 106, which may facilitate removal of the device 100 from the delivery site. In some examples, some or all of the filling material may be removed from the lumen 105, as by providing a suction force at a proximal end of the tubular member 104.

When a desired amount of the filling material 126 has been delivered into the lumen 105 of the tubular member 104, the delivery catheter 124 can be removed from the tubular member 104, and the proximal region 122 of the tubular member 102 remaining external to the balloon member 102 can be sealed. For example, the proximal end of the tubular member 104 may be capped (e.g., by inserting a stopping member at the distal end), clamped, or tied off. In some examples, the proximal region 122 of the tubular member 104 may self-seal upon itself.

Figure 7:
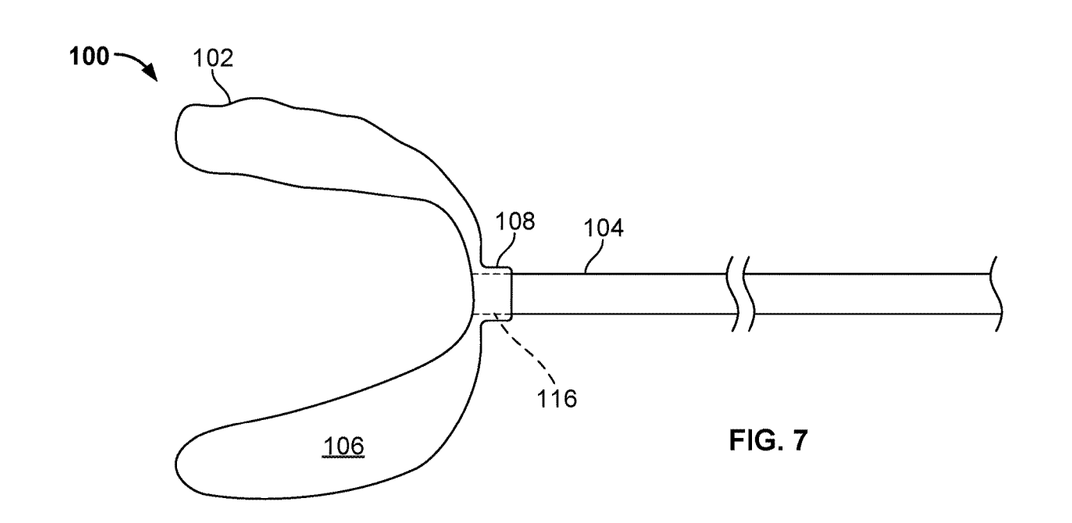
FIG. 7 is a side view of the space-filling device of FIG. 1 being withdrawn from a delivery site.

If appropriate, at a later time following implantation of the space-filling device 100, the space-filling device 100 may be removed or repositioned from the original delivery site by pulling the external portion of the proximal region 122 of the tubular member 104 to cause all but the distal portion 116 of the tubular member 104 to be pulled through the port 108. FIG. 7 shows the device after all but the distal portion 116 of the tubular member 104 has been pulled through the port 108. As can be seen in FIG. 7, the device may return to a substantially collapsed state, and the internal compartment 106 may be substantially empty. The tubular member 104 may extend substantially proximal of the balloon member 102.

Figure 8:
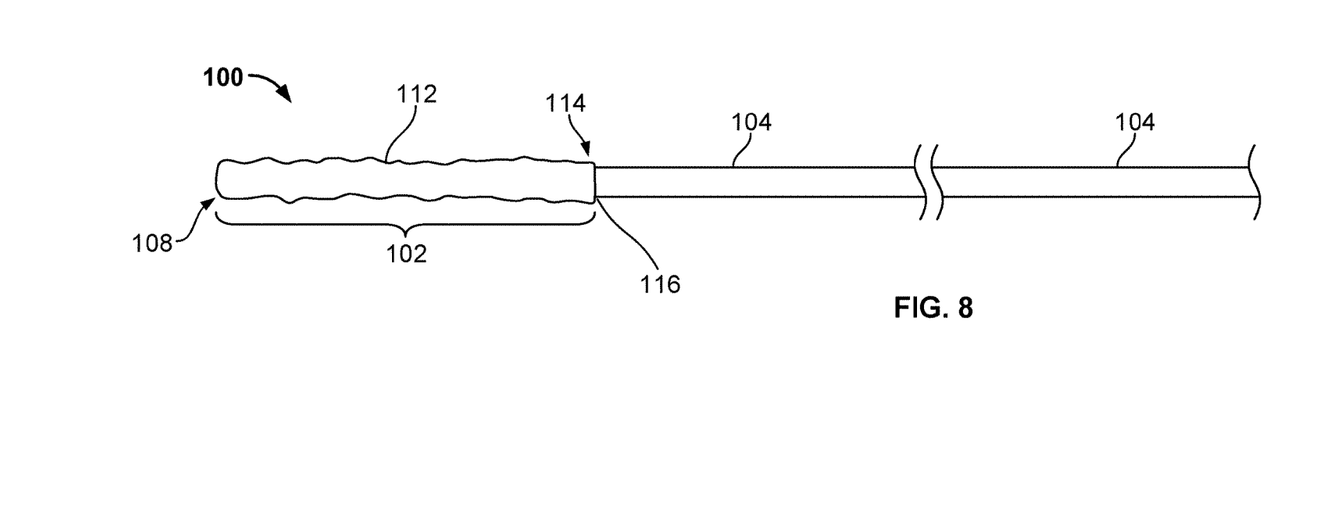
FIG. 8 is a side view of the space-filling device of FIG. 7 after eversion of the balloon.

In some examples, the balloon member 102 may not evert (e.g., as shown in FIG. 7) during withdrawal of the space-filling device. In some examples the distal end 116 of the tubular member 104, attached at the inner surface 112 of the balloon member 102, may be pulled through the port 108, and the balloon member 102 may evert. FIG. 8 shows an example of device removal where the device 100 has everted. For example, the distal end 116 of the tubular member 104 and a substantial portion of the balloon member 102 has been pulled through the port 108. The balloon element 102 and port 108 are withdrawn, along with the tubular member 104, because the tubular member 104 is attached, connected, or integral with a distal end portion 114 of the balloon member 102, as described above with reference to FIG. 1. This may facilitate a convenient and low profile manner of removing the device 100 from the delivery site. In this manner, the space-filling device 100 can be pulled from the delivery site and out of the body.

In some examples, a shape-set NiTi wire may be used to help fill the balloon member 102.

Several characteristics and advantages have been set forth in the preceding description, including various alternatives together with details of the structure and function of the devices and/or methods. The disclosure is intended as illustrative only, and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A method of implanting a space-filling medical device within a body of a patient, the method comprising:
   delivering a medical device to a target site within the body, the medical device configured to occupy a space at the target site, wherein the medical device comprises:
   a vessel member that defines a compartment interior of the vessel member,
   a port, the port coupling the compartment interior and a region exterior of the vessel member, and
   a tubular member that defines a lumen and includes a distal end and a proximal end, the distal end of the tubular member being attached to an internal surface of the vessel member within the compartment so that a portion of the internal surface of the vessel member provides a seal at a distal end of the lumen, wherein the tubular member extends through the port and wherein the proximal end of the tubular member is configured to remain in the region exterior of the vessel member, and wherein the tubular member is configured to receive a filling material delivered into the lumen of the tubular member, and further wherein the vessel member and the tubular member are porous or microporous, and the filling material includes a therapeutic substance that diffuses out of the space-filling device through the pores or micro-pores of the vessel member and the tubular member;

delivering the filling material into the lumen of the tubular member; and coupling a stopping member with the proximal end of the tubular member, wherein at least a portion of the stopping member is sized larger than the port such that the proximal end of the tubular member is prevented from passing through the port and into the compartment interior.

2. A method according to claim 1, wherein the vessel member occupies a first volume prior to the delivery of the filling material into the lumen of the tubular member, and wherein the vessel member occupies a second volume after the delivery of the filling material into the lumen of the tubular member, the second volume being greater than the first volume.

3. A method according to claim 1, further comprising adjusting a buoyancy of the medical device.

4. A method according to claim 3, wherein the lumen of the tubular member carries a first filling material comprising a foam, the method further comprising reducing the buoyancy by delivering a second filling material into the lumen of the tubular member, the second filling material comprising a liquid.

5. A method according to claim 3, wherein the lumen of the tubular member carries a first filling material comprising a foam, the method further comprising increasing the buoyancy by delivering a second filling material into the lumen of the tubular member, the second filling material comprising a gas.

6. A method according to claim 3, further comprising delivering one or more liquids and one or more gasses into the lumen of the tubular member.

7. A method according to claim 1, further comprising coupling the medical device with a delivery catheter, the delivery catheter including a conduit through which the filling material flows into the lumen of the tubular member.

8. A method according to claim 7, further comprising inserting the delivery catheter within the tubular member.

9. A method according to claim 7, further comprising inserting the tubular member within the delivery catheter.

10. A method according to claim 7, wherein the delivery catheter extends into the compartment interior for at least a part of the time while the filling material is delivered into the lumen of the tubular member.

11. A method according to claim 7, further comprising coupling the delivery catheter with a pressurized filling material delivery apparatus, the pressurized filling material delivery apparatus configured to controllably deliver the filling material into the delivery catheter.

12. A method according to claim 1, wherein the proximal end of the tubular member is prevented from passing through the port such that the proximal end of the tubular member remains in the region exterior of the vessel member.

13. A method according to claim 1, wherein the filling material comprises one or more of a liquid, a gas, a foam, a gel, a solid, a radio opaque material, and silicone.

14. A method according to claim 1, wherein the filling material comprises at least one of a bioinert material and a biocompatible material.

15. A method according to claim 1, further comprising removing the medical device from the body by pulling the proximal end of the tubular member in a proximal direction.

16. A method according to claim 1, wherein the vessel member is a balloon device.

17. A method of treating a patient, the method comprising:
delivering a medical device to a target site in the patient, the medical device configured to occupy a space in the patient, wherein the medical device comprises:
a vessel member that defines a compartment interior of the vessel member,
a port attached to the vessel member, the port coupling the compartment interior of the vessel member to a region exterior of the vessel member, and
a tubular member comprising a lumen, a distal end, and a proximal end, wherein the distal end of the tubular member is attached to an internal surface of the vessel member in the compartment interior, wherein the proximal end of the tubular member extends through the port and is releasably attachable to a delivery catheter that has an advancement component for advancing the tubular member into the compartment interior to at least partially fill the vessel member, and wherein the distal end of the tubular member has a seal; and
delivering filling material into the lumen of the tubular member.

18. The method according to claim 17, wherein the delivery of filling material into the lumen of the tubular member causes an additional length of the tubular member to pass through the port and into the compartment interior of the vessel member, the filling material being contained within the lumen of the tubular member.

* * * * *